(12) United States Patent
Wu

(10) Patent No.: US 9,872,832 B2
(45) Date of Patent: Jan. 23, 2018

(54) NANOEMULSIONS HAVING REVERSIBLE CONTINUOUS AND DISPERSED PHASES

(71) Applicant: LG Bionano, LLC, Wilmington, DE (US)

(72) Inventor: Chien-Chin Wu, Wilmington, DE (US)

(73) Assignee: LG Bionano, LLC, Wilmington, DE (US)

( * ) Notice: Subject to any disclaimer, the term of this patent is extended or adjusted under 35 U.S.C. 154(b) by 0 days.

(21) Appl. No.: 14/921,572

(22) Filed: Oct. 23, 2015

(65) Prior Publication Data

US 2017/0112764 A1    Apr. 27, 2017

(51) Int. Cl.

| | | |
|---|---|---|
| C09D 11/02 | (2014.01) |
| A61K 47/18 | (2017.01) |
| B01F 17/00 | (2006.01) |
| A61K 8/00 | (2006.01) |
| A61K 9/107 | (2006.01) |
| A23D 7/005 | (2006.01) |
| A61K 8/06 | (2006.01) |
| A61K 8/34 | (2006.01) |
| A61K 8/36 | (2006.01) |
| A61K 8/37 | (2006.01) |
| A61K 8/40 | (2006.01) |
| A61K 8/46 | (2006.01) |
| A61K 8/60 | (2006.01) |
| A61K 8/891 | (2006.01) |
| A61K 8/92 | (2006.01) |
| A61K 47/12 | (2006.01) |
| A61K 47/14 | (2017.01) |
| A61K 47/16 | (2006.01) |
| A61K 47/20 | (2006.01) |
| A61K 47/26 | (2006.01) |
| A61K 47/34 | (2017.01) |
| A61K 47/44 | (2017.01) |
| A23L 27/00 | (2016.01) |

(52) U.S. Cl.
CPC .......... *A61K 9/1075* (2013.01); *A23D 7/0053* (2013.01); *A23L 27/80* (2016.08); *A61K 8/00* (2013.01); *A61K 8/068* (2013.01); *A61K 8/345* (2013.01); *A61K 8/361* (2013.01); *A61K 8/375* (2013.01); *A61K 8/40* (2013.01); *A61K 8/46* (2013.01); *A61K 8/602* (2013.01); *A61K 8/891* (2013.01); *A61K 8/922* (2013.01); *A61K 8/925* (2013.01); *A61K 47/12* (2013.01); *A61K 47/14* (2013.01); *A61K 47/16* (2013.01); *A61K 47/18* (2013.01); *A61K 47/20* (2013.01); *A61K 47/26* (2013.01); *A61K 47/34* (2013.01); *A61K 47/44* (2013.01); *B01F 17/00* (2013.01); *C09D 11/02* (2013.01)

(58) Field of Classification Search
None
See application file for complete search history.

(56) References Cited

U.S. PATENT DOCUMENTS

| | | | |
|---|---|---|---|
| 7,488,471 B2 | 2/2009 | Merciet et al. | |
| 2004/0067244 A1 | 4/2004 | Friedman | |
| 2006/0193813 A1* | 8/2006 | Simonnet | A61K 8/06 424/70.21 |
| 2008/0138296 A1* | 6/2008 | Tamarkin | A61K 8/046 424/47 |
| 2010/0216751 A1* | 8/2010 | Jacob | A61K 9/0095 514/169 |
| 2011/0039950 A1* | 2/2011 | Behler | A61K 8/06 514/777 |
| 2012/0052126 A1 | 3/2012 | Pathak et al. | |

FOREIGN PATENT DOCUMENTS

| | | |
|---|---|---|
| EP | 2000130 A1 | 12/2008 |
| JP | H06507172 A | 8/1994 |
| JP | H08504759 A | 5/1996 |
| WO | WO-2007/094605 A1 | 8/2007 |

OTHER PUBLICATIONS

New Alternatives to Cosmetics Preservation ([retrieved from on-line website: https://www.personalcaremagazine.com/story/8736/suppliers, Sep. 7, 2011]).*
Naturallycurly ([retrieved from on-line website: https://www.naturallycurly.com/curlreading/curl-products/curlchemist-the-truth-and-fiction-about-propylene-glycol/, publicly available since Nov. 9, 2010]).*
Dou et al., "Modification of Thermal and Mechanical Properties of PEG-PPG-PEG copolymer (F127) with MA-Poss", Polymers 2016, 8, 341, pp. 1-14.*
ICI Americas Inc. "The HLB System—A Time-Saving Guide to Emulsifier Selection" pp. 1-22. 1980.
Akzo Nobel Surface Chemistry LLC "HLB & Emulsification—Description of Hydrophile, Lipophile Balance and Use of HLB in Producing Emulsions" pp. 1-15. 2011.
Shah et al "Nanoemulsion: A Pharmaceutical Review" Systematic Reviews in Pharmacy vol. 1, pp. 24-32, 2010.

* cited by examiner

*Primary Examiner* — Ernst V Arnold
*Assistant Examiner* — Kyung Sook Chang
(74) *Attorney, Agent, or Firm* — Cesari and McKenna, LLP

(57) ABSTRACT

A nanoemulsion having reversible continuous and dispersed phases. The nanoemulsion includes an aqueous phase and an oil phase, a weight ratio of the aqueous phase to the oil phase being 1:40-100:1. In the nanoemulsion, the aqueous phase is dispersed as nanosized droplets in the oil phase or the oil phase is dispersed as nanosized droplets in the aqueous phase. The aqueous phase contains water or a water solution and a water-soluble organic nanostructure stabilizer. The oil phase contains an oil or an oil solution, an organic gel thickener, and a hydrophilic surfactant having a hydrophilic-lipophilic balance value greater than 8.0. Also disclosed is a method for preparing the above-described nanoemulsion.

22 Claims, No Drawings

NANOEMULSIONS HAVING REVERSIBLE CONTINUOUS AND DISPERSED PHASES

BACKGROUND

There are two types of nanoemulsions, i.e., an oil-in-water (o/w) nanoemulsion and a water-in-oil (w/o) nanoemulsion. An o/w nanoemulsion has a continuous water phase and a dispersed oil phase while a w/o nanoemulsion has a continuous oil phase and a dispersed water phase.

These two types of nanoemulsions are stabilized by emulsifiers that have different hydrophilic-lipophilic balance (HLB) values. An o/w nanoemulsion is stabilized by an emulsifier having a HLB value of 8-28 and a w/o emulsion is stabilized by an emulsifier having a HLB value of 3-6. As a result, they cannot be easily inter-converted.

The lack of facile convertibility can be problematic. An o/w nanoemulsion collapses when its water content decreases. Similarly, a w/o nanoemulsion collapses when its oil content decreases.

Thus, there is a need to develop a nanoemulsion that its continuous phase and dispersed phase can be readily converted from one to the other with the same emulsifier contained in it.

SUMMARY OF THE INVENTION

Disclosed herein is a nanoemulsion containing reversible continuous and dispersed phases.

The nanoemulsion of this invention includes an aqueous phase and an oil phase, a weight ratio of the aqueous phase to the oil phase being 1:40-100:1. In the nanoemulsion, the aqueous phase is dispersed as nanosized droplets in the oil phase or the oil phase is dispersed as nanosized droplets in the aqueous phase. The aqueous phase, which constitutes 2.5% by weight or more of the nanoemulsion, contains water or a water solution (e.g., containing a water-soluble active ingredient) and a water-soluble organic nanostructure stabilizer. The water or water solution has a content less than 75% by weight of the aqueous phase and the water-soluble organic nanostructure stabilizer has a content less than 99% by weight of the aqueous phase. The oil phase contains an oil or an oil solution, an organic gel thickener, and a hydrophilic surfactant having a HLB value greater than 8.0. The oil or oil solution (e.g., containing an oil-soluble active ingredient) has a content less than 80% by weight of the oil phase, the organic gel thickener has a content less than 60% by weight of the oil phase, and the hydrophilic surfactant has a content less than 60% by weight of the oil phase. This nanoemulsion can be used as a carrier of an active ingredient in a cosmetic, food, or pharmaceutical composition.

Also within the scope of this invention is a method for preparing the above-described nanoemulsion. The method includes the following steps: (1) mixing water or a water solution and a water-soluble organic nanostructure stabilizer to form an aqueous phase, in which the water or water solution has a content less than 75% by weight of the aqueous phase and the water-soluble organic nanostructure stabilizer has a content less than 99% by weight of the aqueous phase; (2) mixing an oil or an oil solution, an organic thickener, and a hydrophilic surfactants having a hydrophilic-lipophilic balance value greater than 8.0 to form an oil phase, in which the oil or oil solution has a content less than 80% by weight of the oil phase, the organic gel thickener has a content less than 60% by weight of the oil phase, and the hydrophilic surfactant has a content less than 60% by weight of the oil phase; and (3) mixing the aqueous phase and the oil phase, a weight ratio of the aqueous phase to the oil phase being 1:40-100:1, to form a nanoemulsion, in which the water or water solution constitutes 74% by weight or less of the nanoemulsion. Each of the mixing steps is performed at a suitable temperature, e.g., 5-95° C.

In the thusly prepared nanoemulsion, the aqueous phase is dispersed as nanosized droplets in the oil phase or the oil phase is dispersed as nanosized droplets in the aqueous phase. Put differently, continuous and dispersed phases in the nanoemulsion are reversible.

The details of one or more embodiments are set forth in the description below. Other features, objects, and advantages of the embodiments will be apparent from the description and the claims.

DETAILED DESCRIPTION

The present invention is based on, at least in part, an unexpected finding that a nanoemulsion, containing a hydrophilic surfactant having a HLB value greater than 8, can have either the aqueous phase dispersed as nanosized droplets in the oil phase or the oil phase dispersed as nanosized droplets in the aqueous phase. In other words, the nanoemulsion has reversible continuous and dispersed phases.

This nanoemulsion can carry both oil-soluble active ingredients and water-soluble active ingredients, an advantage over conventional nanoemulsions. The advantage is especially important in preparing cosmetic, food, household chemical, agricultural, printing, dying, veterinary, diagnostic, vaccine, and pharmaceutical products, as demonstrated by the two following examples.

An o/w emulsion is preferably used in a cosmetic product, as it is less sticky and greasy than a w/o emulsion and has a desirable water-holding ability. However, when a cosmetic product is applied to the skin or exposed to air, the nanoemulsion in the cosmetic product loses water through evaporation. Water loss causes collapse of a conventional o/w nanoemulsion, but not an o/w nanoemulsion of this invention. Instead, the latter nanoemulsion slowly converts to a w/o nanoemulsion in which its water phase is uniformly dispersed as nanosized droplets in its oil phase.

Differently, for an oil-soluble drug, a w/o emulsions is preferably used due to its high loading capacity. However, as body fluids are aqueous, when a w/o nanoemulsion comes into contact with the body fluids, its water content inevitably increases. As a result, the conventional w/o nanoemulsion collapses. Yet, the w/o nanoemulsion of this invention slowly converts to an o/w nanoemulsion in which its oil phase is uniformly dispersed as nanosized droplets in its water phase. Notably, the conversion not only maintains the integrity of a nanoemulsion but also provides a sustained-release of the drug in it.

As pointed out above, the nanoemulsion of this invention includes an aqueous phase and an oil phase. In the nanoemulsion, the aqueous phase can be dispersed as nanosized droplets in the oil phase. Alternatively, the oil phase can be dispersed as nanosized droplets in the aqueous phase.

The aqueous phase includes a water-soluble organic nanostructure stabilizer. The term "water-soluble organic nanostructure stabilizer" herein refers to any water-soluble organic ingredient that can stabilize the isotropic structure of a nanoemulsion, thereby resulting in a thermodynamically stable transparent or translucent nanoemulsion. It can be a water-soluble vitamin, a water-soluble peptide, a water-soluble oligopepetide, a polyol, a water-soluble saccharide, a water-soluble oligosaccharide, a disaccharide, a monosaccharides, a hydrogenated carbohydrate, an amino acid, an amino sugar, or a combination thereof. Specific examples include urea, methylsulfonylmethane, hydroxyethyl urea, glucosamine, mannitol, sorbitol, xylitol, lactose, fructose, dextrose, ribose, trehalose, raffinose, maltitol, isomalt, lactitol, erythritol, inositol, taurine, glycerin, propylene glycol, dipropylene glycol, butylene glycol, hexylene glycol, polyethylene glycol, ethoxydiglycol, carntine, arginine, sodium pyrrolidone carboxylic acid, and hydrolyzed collagen.

The oil phase contains an oil or an oil solution. A vegetable oil, a silicone oil, a synthetic oil, a mineral oil, an animal oil, an essential oil, or a combination thereof can be used to form the oil phase. Specific examples include coconut oil, palm oil, grape seed oil, olive, oil, grape fruit seed oil, flaxseed oil, avocado oil, evening primrose oil, lavender oil, rosemary oil, tea tree oil, eucalyptus oil, horse fat, fish oils, lanolin oil, squalene, cyclomethicon, cyclopentasilaxone, phenyl trimethicone, caprylic/capric triglyceride, isopropyl myristate, isostearyl isostearate, decyl oleate, ethylhexyl isonononate, isohexadecane, octyldodecanol, paraffin oil, polydecene, polyisobutene, menthol, or a combination thereof. Note that the oil solution contains one or more oils as solvents for dissolving one or more oil-soluble solutes.

As also pointed out above, the oil phase includes a hydrophilic surfactant having a HLB value greater than 8.0. Preferably, the HLB value of the hydrophilic surfactant is greater than 10 and, more preferably, the HLB value is greater than 13. Examples of the hydrophilic surfactant include polyoxyethylene sorbitan fatty acid ester (e.g., Tween 20, Tween 21, Tween 60, Tween 61, Tween 65, Tween 80, Tween 81, or Tween 85), polyoxyethylene sorbitol fatty acid ester, polyoxyethylene fatty acid ester (e.g., Myri 45, Myri 52, Myri 53, or Myri 59), polyoxyethylene alcohol ester (e.g., Brij 30, Brij 35, Brij 56, Brij 58, Brij 76, Brij 78, Brij 96, Brij 97, Brij 98, or Brij 99), nonyl phenol alkoxylate (e.g., Witconol™ nonyl phenol based nonionic surfactant), alkyl alkoxylate (e.g., Ethylan™ family nonionic surfactant), Pluronic F-127, PEG dimethicone, polyoxyethylene (40) fatty acid ester, polyoxyethylene (20) saccharide fatty acid ester, PEG-15 glyceryl fatty acid ester, PEG-35 hydrogenated castor oil, PEG-40 hydrogenated castor oil, polyglycerol fatty acid ester, a fatty amine derivative, or a combination thereof.

Further, the oil phase contains an organic gel thickener. The term "organic gel thickener" herein refers to any substance that raises the viscosity and causes structural formation of a nanoemulsion. The organic gel thickener can be saturated fatty acid, fatty acid alcohol, a fatty acid derivative having a melting point above 45° C., or a combination thereof. Examples of the organic gel thickener include stearic acid, lauric acid, glycerol monostearate, PEG 6000 diesterate, monoglyceride, diglyceride, saccharide fatty acid ester, propylene glycol fatty acid ester, glycol fatty acid ester, hexyl decyl fatty acid ester, fatty acid alcohol, cetyl sterate, ascorbyl fatty ester, glyceryl fatty ester, hexyldecyl fatty ester or a combination thereof.

In one embodiment, the water or water solution of the nanoemulsion of this invention has a content less than 60% by weight of the aqueous phase and the water-soluble organic nanostructure stabilizer has a content less than 70% by weight of the aqueous phase; the oil or oil solution has a content 30-70% by weight of the oil phase, the organic gel thickener has a content less than 45% by weight of the oil phase, and the hydrophilic surfactant has a content less than 45% by weight of the oil phase; and the water or water solution constitutes 38% by weight or less of the nanoemulsion and a weight ratio of the aqueous phase to the oil phase is 1:3-4:1. Preferably, the water or water solution has a content less than 45% by weight of the aqueous phase and the water-soluble organic nanostructure stabilizer has a content less than 50% by weight of the aqueous phase; the oil or oil solution has a content less than 45-65% by weight of the oil phase, the organic gel thickener has a content less than 25% by weight of the oil phase, and the hydrophilic surfactant has a content less than 35% by weight of the oil phase; and the water or water solution constitutes 30% by weight or less of the nanoemulsion and a weight ratio of the aqueous phase to the oil phase is 1:2-3:1.

The nanoemulsion of this invention is transparent or translucent in solid gel form or liquid form at a pH of 3-11. In addition, it exhibits a nano characteristic, i.e., Tyndall light refraction effect. See Gold and Silver Nanoparticles, Center for Nanoscale Chemical-Electrical-Mechanical Manufacturing Systems, University of Illinois, http://Nano-cemms.illinois.edu/media/content/teaching_mats/online/gold_and_silver_nanoparticles/docs/presentation.pdf.

The nanoemulsion of this invention whose water or water solution constitutes 38% by weight or less of the nanoemulsion has a self-preserving ability and, as such, there is no need to include an anti-microbial preservative in it. A preservative usually raises safety concerns, as it may pose health hazards ranging from a mild headache to the most serious diseases, e.g., cancer.

When used in cosmetic, food and pharmaceutical compositions, this nanoemulsion can carry various active ingredients, e.g., terbinafine, diclofenanc diethylamine, capsaicin, diazepam, lorazepam, propofol, metronidazole, indomethacine, clotrimazole, ketoconazole, erythrolmycin, clibazole, kinetin, bifonazole, miconazole, tonalftate, clobetasol, econazole, bezocaine, phenytoin, lovastatin, isosorbide dinitrate, nitroglycerin, farmotidine, bisabodol, lutein ester, melatonin, oil-soluble vitamins, lycopene, resveratrol, ginsenoisides, vanillyl butyl ether, curcumin, and CoQ10. A nanoemulsion including a drug can be administered via various routes, e.g., oral, topical, virginal, rectal, sublingual, pulmonary, and parenteral. If desired, certain sweetening, flavoring, coloring agents or fragrances can also be added.

The method of this invention for preparing the above-described nanoemulsion includes first forming an aqueous phase and an oil phase separately, and then mixing the two phases. Water or a water solution and a water-soluble organic nanostructure stabilizer can be mixed by constant stirring (manually or otherwise), high-speed and high-shear mixing (e.g., using a colloid mill), high-pressure mixing (e.g., using a micro fluidizer), or sonication mixing to form the aqueous phase. An oil or an oil solution, an organic thickener, and a hydrophilic surfactants can also be thus mixed to form the oil phase. The resulting aqueous phase and oil phase can then be mixed in a similar manner to form a nanoemulsion. Of note, all the mixing steps can be performed at an elevated temperature, e.g., 45-85° C., if needed. Importantly, the oil phase and aqueous phase thus obtained can be used to prepare either an o/w nanoemulsion or a w/o nanoemulsion, indicating that the continuous and dispersed phases are reversible.

Without further elaboration, it is believed that the above description has adequately enabled the present invention. The following examples are, therefore, to be construed as merely illustrative, and not limitative of the remainder of the disclosure in any way whatsoever. The publication cited herein is hereby incorporated by reference in its entirety.

Example 1: Determination of the Type of a Nanoemulsion 60 ml of water was placed in a 100-ml beaker. A nanoemulsion to be tested was added dropwise to the water. If the nanoemulsion dispersed in the water giving rise to a clear or translucent solution, the tested nanoemulsion was an o/w nanoemulsion. However, if the nanoemulsion formed oil-like droplets in the water, the tested nanoemulsion was a w/o nanoemulsion.

Example 2: Preparation of Coconut Oil Nanoemulsions

The nanoemulsions were prepared following the procedure described below.
Preparation of the Aqueous Phase of the Nanoemulsions A combination of 210 gm of purified water, 90 gm of urea, 60 gm of xylitol, 60 gm of Trehalose, and 30 gm of methyl sulfonyl methane was mixed by constant manual stirring in a 500-ml beaker at 65-75° C. to form the aqueous phase.
Preparation of the Oil Phase of the Nanoemulsions A combination of 80 gm of coconut oil, 20 gm of paraffin oil, 50 gm of cyclomethicone (DC-345), 20 gm of beeswax, 10 gm of glyceryl monostearate, 16 gm of stearic acid, 14 gm of sorbitan monostearate, 36 gm of polyethylene glycol sorbitan monostearate, and 42 gm of PEG-40 hydrogenated castor oil was mixed by constant manual stirring in a 500-ml beaker at 65-75° C. to form the oil phase.
Preparation of the Nanoemulsions A combination of the oil phase and the aqueous phase prepared above at a weight ratio shown in Table 1 was mixed by constant manual stirring in a 200-ml beaker at 65-75° C. for less than 0.5 hours to form a w/o or an o/w nanoemulsion.

TABLE 1

| | ID | | | |
|---|---|---|---|---|
| | 1 | 2 | 3 | 4 |
| Oil phase (gm) | 120 | 90 | 40 | 25 |
| Aqueous phase (gm) | 30 | 60 | 60 | 75 |
| Nanoemulsion (gm) | 150 | 150 | 100 | 100 |
| Type | w/o | w/o | o/w | o/w |
| Physical appearance | Translucent | Clear | Clear | Clear |

All the nanoemulsions were stable at room temperature for at least 3 months and exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and all of the nanoemulsions prepared in this example passed this antimicrobial test.

Example 3: Preparation of Palm Oil Nanoemulsions

The nanoemulsions were prepared following the procedure described below.

150 gm of a w/o nanoemulsion composed of 30 gm of the aqueous phase and 120 gm of the oil phase was prepared following the procedure described in Example 2 except that palm oil was used instead of coconut oil. The nanoemulsion thusly prepared was translucent and stable at room temperature for at least 3 months. It exhibited the Tyndall light refraction effect.

150 gm of a w/o nanoemulsion composed of 60 gm of the aqueous phase and 90 gm of the oil phase was prepared following the procedure described in Example 2 except that palm oil was used instead of coconut oil. The nanoemulsion thusly prepared was clear and stable at room temperature for at least 3 months. It exhibited the Tyndall light refraction effect.

150 gm of an o/w nanoemulsion composed of 60 gm of the aqueous phase and 90 gm of the oil phase was prepared following the procedure described in Example 2 except that palm oil was used instead of coconut oil. The nanoemulsion thusly prepared was clear and stable at room temperature for at least 3 months. It exhibited the Tyndall light refraction effect.

100 gm of an o/w nanoemulsion composed of 75 gm of the aqueous phase and 25 gm of the oil phase was prepared following the procedure described in Example 2 except that palm oil was used instead of coconut oil. The nanoemulsion thusly prepared was clear and stable at room temperature for at least 3 months. It exhibited the Tyndall light refraction effect.

The type of each nanoemulsion prepared in this example was determined following the procedure described in Example 1.

All of the nanoemulsions prepared in this example passed an antimicrobial test, which was conducted following the procedure described in USP 35 <51>, Antimicrobial Effectiveness Testing, at page 52.

Example 4: Preparation of Horse Fat Nanoemulsions

The nanoemulsions were prepared following the procedure described below.

150 gm of a w/o nanoemulsions composed of 60 gm of the aqueous phase and 90 gm of the oil phase was prepared following the procedure described in Example 2 except that horse fat was used instead of coconut oil.

100 gm of an o/w nanoemulsion composed of 60 gm of the aqueous phase and 40 gm of the oil phase was prepared following the procedure described in Example 2 except that horse fat was used instead of coconut oil.

The thusly prepared nanoemulsions were clear and stable at room temperature for at least 3 months. They both exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and both of the nanoemulsions prepared in this example passed this antimicrobial test.

Example 5: Preparation of Horse Fat Nanoemulsions

The nanoemulsions were prepared following the procedure described below.
Preparation of the Aqueous Phase of the Nanoemulsions A combination of 150 gm of purified water, 150 gm of urea, and 40 gm of mannitol was mixed by constant manual stirring in a beaker at 65-75° C. to form the aqueous phase.
Preparation of the Oil Phase of the Nanoemulsions The oil phase was prepared following the procedure described in Example 2 except that horse fat was used instead of coconut oil.

Preparation of the Nanoemulsions 150 gm of a w/o nanoemulsion composed of 60 gm of the aqueous phase and 90 gm of the oil phase was prepared following the procedure described in Example 2.

100 gm of an o/w nanoemulsion composed of 60 gm of the aqueous phase and 40 gm of the oil phase was prepared following the procedure described in Example 2.

The thusly prepared nanoemulsions were clear and stable at room temperature for at least 3 months. They both exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and the two nanoemulsions prepared in this example passed this antimicrobial test.

Example 6: Preparation of Palm Oil/Squalene Nanoemulsions Containing Only One Hydrophilic Surfactant The nanoemulsions were prepared following the procedure described below.

Preparation of the Aqueous Phase of the Nanoemulsions

A combination of 180 gm of purified water, 100 gm of urea, 20 gm of butylene glycol was mixed by constant manual stirring in a 500-ml beaker at 65-75° C. placed to form the aqueous phase.

Preparation of the Oil Phase of the Nanoemulsions

A combination of 100 gm of palm oil, 20 gm of squalene, 25 gm of cyclomethicon (DC-345), 10 gm of beeswax, 20 gm of stearic acid, 16 gm of sorbitan monostearate, and 60 gm of PEG-40 hydrogenated castor oil was mixed by constant manual stirring in a 500-ml beaker at 65-75° C. to form the oil phase.

Preparation of the Nanoemulsions

A combination of the oil phase and the aqueous phase prepared above at a weight ratio shown in Table 2 was mixed by constant manual stirring in a 500-ml beaker at 65-75° C. for up to 0.5 hours to form a nanoemulsion also listed in Table 2.

TABLE 2

| | ID | | | |
|---|---|---|---|---|
| | 1 | 2 | 3 | 4 |
| Oil Phase (gm) | 105 | 90 | 60 | 30 |
| Aqueous Phase (gm) | 15 | 60 | 90 | 120 |
| Total weight (gm) | 120 | 150 | 150 | 150 |
| Type | w/o | w/o | o/w | o/w |
| Physical appearances | Translucent | Clear | Clear | Clear |

All of the above nanoemulsions were stable at room temperature for at least 3 months and exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and all of the nanoemulsions prepared in this example passed this antimicrobial test.

Example 7: Preparation of Coconut Oil-Based Pharmaceutical Nanoemulsions

The nanoemulsions were prepared following the procedure described below.

50 gm of an o/w nanoemulsion composed of 29.5 gm of the aqueous phase 20 gm of the oil phase dissolving 0.5 gm of one oil-soluble pharmaceutically active ingredient was prepared following the procedure described in Example 2. The oil-soluble pharmaceutically active ingredient is terbinafine, diclofenac diethylamine, diethylamine, metronidazole, indomethacine, clotrimazole, or erythromycin.

The thusly prepared six nanoemulsions were clear and stable at room temperature for at least 3 months. They exhibited the Tyndall light refraction effect.

The type of each nanoemulsions prepared in this example was determined following the procedure described in Example 1.

An antimicrobial test was conducted following the procedure described in USP 35 <51>, Antimicrobial Effectiveness Testing, at page 52, and all of the nanoemulsions prepared in this example passed this antimicrobial test.

Example 8: Preparation of Palm Oil-Based Pharmaceutical Nanoemulsions

The nanoemulsions were prepared following the procedure described in Example 7 except that palm oil was used instead of coconut oil and the oil-soluble pharmaceutically active ingredient is terbinafine, diclofenac diethylamine, metroconazole, kinetin, bifonazole, and miconazole.

The thusly prepared six nanoemulsions were clear and stable at room temperature for at least 3 months. They exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and all of the nanoemulsions prepared in this example passed this antimicrobial test.

Example 9: Preparation of Essential Oil Nanoemulsions Containing Climbazole

The nanoemulsions were prepared following the procedure described below.

Preparation of the Aqueous Phase of the Nanoemulsions

A combination of 150 gm of purified water, 150 gm of urea, and 40 gm of propylene glycol was mixed by constant manual stirring in a 500-ml beaker at 65-75° C. to form the aqueous phase.

Preparation of the Oil Phase of the Nanoemulsions

A combination of 40 gm of tea tree oil, 20 gm of eucalyptus oil, 30 gm of menthol, 50 gm of paraffin oil, 50 gm of cyclomethicone (DC-345), 20 gm of beeswax, 10 gm of glyceryl monostearate, 16 gm of stearic acid, 14 gm of sorbitan monostearate, 36 gm of polyethylene glycol sorbitan monostearate, and 42 gm of PEG-40 hydrogenated castor oil was mixed in a 500-ml beaker by constant manual stirring at 65-75° C. to form the oil phase.

Preparation of the Nanoemulsions 150 gm of a w/o nanoemulsion composed of 60 gm of the aqueous phase and 90 gm of the oil phase was prepared following the procedure described in Example 2.

150 gm of an o/w nanoemulsion composed of 90 gm of the aqueous phase and 60 gm of the oil phase was prepared following the procedure described in Example 2.

100 gm of an o/w nanoemulsion composed of 59 gm of the aqueous phase dissolving 1 gm of climbazole and 40 gm of the oil phase was prepared following the procedure described in Example 2.

All of the above nanoemulsions were clear and stable at room temperature for at least 3 months. They exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and all of the nanoemulsions prepared in this example passed this antimicrobial test.

Example 10: Preparation of Essential Oil Nanoemulsions Having an Aqueous Phase Different from that in Example 9

The nanoemulsions were prepared following the procedure described below.

Preparation of the Aqueous Phase of the Nanoemulsions

A combination of 210 gm of purified water, 90 gm of urea, 60 gm of xylitol, 60 gm of trehalose, and 30 gm of methyl sulfonyl methane was mixed by constant manual stirring in a 500-ml beaker at 65-75° C. to form the aqueous phase.

Preparation of the Oil Phase of the Nanoemulsions

A combination of 40 gm of tea tree oil, 20 gm of eucalyptus oil, 30 gm of menthol, 50 gm of paraffin oil, 50 gm of cyclomethicone (DC-345), 20 gm of beeswax, 10 gm of glyceryl monostearate, 16 gm of stearic acid, 14 gm of sorbitan monostearate, 36 gm of polyethylene glycol sorbitan monostearate, and 42 gm of PEG-40 hydrogenated castor oil was mixed by constant manual stirring in a 500-ml beaker at 65-75° C. to form the oil phase.

Preparation of the Nanoemulsions 150 gm of a w/o nanoemulsion composed of 60 gm of the aqueous phase and 90 gm of the oil phase was prepared following the procedure described in Example 2.

150 gm of an o/w nanoemulsion composed of 90 gm of the aqueous phase and 60 gm of the oil phase was prepared following the procedure described in Example 2.

The two nanoemulsions were clear and stable at room temperature for at least 3 months. Both of them exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and both nanoemulsions prepared in this example passed this antimicrobial test.

Example 11: Preparation of Essential Oil Nanoemulsions Containing Tolnaftate or Ketoconazole The nanoemulsions were prepared following the procedure described below.

Preparation of the Aqueous Phase of the Nanoemulsions

A combination of 150 gm of purified water, 150 gm of urea, and 40 gm of propylene glycol was mixed by constant manual stirring in a 500-ml beaker at 65-75° C. to form the aqueous phase.

Preparation of the Oil Phase of the Nanoemulsions

A combination of 50 gm of tea tree oil, 20 gm of eucalyptus oil, 15 gm of menthol, 15 gm of methyl salicylate, 50 gm of cyclomethicone (DC-345), 10 gm of beeswax, 10 gm of lauric acid, 6 gm of stearic acid, 14 gm of Sorbitan monostearate, 40 gm of polyoxyethylene glycol (40) stearate, and 40 gm of PEG-40 hydrogenated castor oil was mixed by constant manual stirring in a 500-ml beaker at 65-75° C. to form the oil phase.

Preparation of the Nanoemulsions 150 gm of a w/o nanoemulsion composed of 60 gm of the aqueous phase and 90 gm of the oil phase was prepared following the procedure described in Example 2.

150 gm of an o/w nanoemulsion composed of 90 gm of the aqueous phase and 60 gm of the oil phase was prepared following the procedure described in Example 2.

150 gm of a w/o nanoemulsion composed of 60 gm of the aqueous phase and 88.2 gm of the oil phase dissolving 1.8 gm of tolnaftate was prepared following the procedure described in Example 2.

150 gm of a w/o nanoemulsion composed of 60 gm of the aqueous phase and 88.2 gm of the oil phase dissolving 1.8 gm of ketoconazole was prepared following the procedure described in Example 2.

All of the above nanoemulsions were clear and stable at room temperature for at least 3 months. They exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and all of the nanoemulsions prepared in this example passed this antimicrobial test.

Example 12: Preparation of Fragrance/Essential Oil Nanoemulsions

The nanoemulsions were prepared following the procedure described below.

Preparation of the Aqueous Phase of the Nanoemulsions

A combination of 150 gm of purified water, 150 gm of urea, and 40 gm of propylene glycol was mixed by constant manual stirring in a 500-ml beaker at 65-75° C. to form the aqueous phase.

Preparation of the Oil Phase of the Nanoemulsions

A combination of 80 gm of lemon eucalyptus oil, 40 gm of citrinella oil, 24 gm of lavander oil, 22 gm of eucalyptus oil, 15 gm of rosemary oil, 15 gm of camphor, 15 gm of menthol, 6 gm of thyme, 10 gm of beeswax, 10 gm of lauric acid, 6 gm of stearic acid, 14 gm of Sorbitan monostearate, 40 gm of polyoxyethylene glycol (40) stearate, and 40 gm of PEG-40 hydrogenated castor oil was mixed by constant manual stirring in a 500-ml beaker at 65-75° C. to form the oil phase.

Preparation of the Nanoemulsions 150 gm of a w/o nanoemulsion composed of 60 gm of the aqueous phase and 90 gm of the oil phase was prepared following the procedure described in Example 2.

100 gm of an o/w nanoemulsion composed of 60 gm of the aqueous phase and 40 gm of the oil phase was prepared following the procedure described in Example 2.

Both nanoemulsions were clear and stable at room temperature for at least 3 months. They exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and the two nanoemulsions prepared in this example passed this antimicrobial test.

Example 13: Preparation of Medium-Chain Oil Nanoemulsions Containing CoQ10

The nanoemulsions were prepared following the procedure described below.

Preparation of the Aqueous Phase of the Nanoemulsions

A combination of 150 gm of purified water, 100 gm of glycerin, 80 gm of xylitol, 20 gm of mannitol, and 30 gm of methyl sulfonyl methane was mixed by constant manual stirring in a 500-ml beaker at 65-75° C. to form the aqueous phase.

Preparation of the Oil Phase of the Nanoemulsions

A combination of 170 gm of medium-chain triglyceride oil, 16 gm of stearic acid, 14 gm of sorbitan monostearate, 30 gm of polyethylene glycol sorbitan monostearate, and 30 gm of PEG-40 hydrogenated castor was mixed by constant manual stirring in a 500-ml beaker at 65-75° C. to form the oil phase.

Preparation of the Nanoemulsions 150 gm of a w/o nanoemulsion composed of 50 gm of the aqueous phase and 95 gm of the oil phase dissolving 5 gm of CoQ10 was prepared following the procedure described in Example 2.

150 gm of an o/w nanoemulsion composed of 90 gm of the aqueous phase and 57 gm of the oil phase dissolving 3 gm of CoQ10 was prepared following the procedure described in Example 2.

153 gm of an o/w nanoemulsion composed of 120 gm of the aqueous phase and 30 gm of the oil phase dissolving 3 gm of CoQ10 was prepared following the procedure described in Example 2.

All of the above nanoemulsions were clear and stable at room temperature for at least 3 months. They exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and all of the nanoemulsions prepared in this example passed this antimicrobial test.

Example 14: Preparation of Medium-Chain Triglyceride Nanoemulsions

The nanoemulsions were prepared following the procedure described below.

Preparation of the Aqueous Phase of the Nanoemulsions

A combination of 100 gm of purified water, 100 gm of glycerin, 50 gm of xylitol, 50 gm of trehalose, 30 gm of erythritol, and 15 gm of maltodextrin was mixed by constant manual stirring in a 500-ml beaker at 65-75° C. to form the aqueous phase.

Preparation of the Oil Phase of the Nanoemulsions

A combination of 170 gm of medium-chain triglyceride, 16 gm of stearic acid, 14 gm of sorbitan monostearate, 30 gm of polyethylene glycol sorbitan monostearate, and 30 gm of PEG-40 hydrogenated castor oil was mixed by constant manual stirring in a 500-ml beaker at 65-75° C. to form the oil phase.

Preparation of the Nanoemulsions 180 gm of a w/o nanoemulsion composed of 54 gm of the aqueous phase and 120 gm of the oil phase dissolving 6 gm of lutein was prepared following the procedure described in Example 2.

300 gm of an o/w nanoemulsion composed of 174 gm of the aqueous phase and 120 gm of the oil phase dissolving 6 gm of lutein was prepared following the procedure described in Example 2.

The nanoemulsions both were clear and stable at room temperature for at least 3 months. They exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and both of the nanoemulsions prepared in this example passed this antimicrobial test.

Example 15: Preparation of Medium-Chain Triglyceride Oil Nanoemulsions Containing CoQ10

The nanoemulsions were prepared following the procedure described below.

Preparation of the Aqueous Phase of the Nanoemulsions

A combination of 100 gm of purified water, 100 gm of glycerin, 50 gm of xylitol, 50 gm of trehalose, 35 gm of erythritol, and 15 gm of maltodextrin was mixed by constant manual stirring in a 500-ml beaker at 65-75° C. to form the aqueous phase.

Preparation of the Oil Phase of the Nanoemulsions

A combination of 50 gm of medium-chain triglyceride, 50 gm of fish oil, 10 gm of stearic acid, 8 gm of sorbitan monostearate, 20 gm of polyethylene glycol sorbitan monostearate, and 20 gm of PEG-40 hydrogenated castor oil was mixed by constant manual stirring in a 500-ml beaker at 65-75° C. to form the oil phase.

Preparation of the Nanoemulsions 125 gm of a w/o nanoemulsion composed of 20 gm of the aqueous phase and 100 gm of the oil phase dissolving 5 gm of CoQ10 was prepared following the procedure described in Example 2.

100 gm of an o/w nanoemulsion composed of 58 gm of the aqueous phase and 40 gm of the oil phase dissolving 2 gm of CoQ10 was prepared following the procedure described in Example 2.

The nanoemulsions both were clear and stable at room temperature for at least 3 months. They exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and all of the nanoemulsions prepared in this example passed this antimicrobial test.

Example 16: Preparation of Squalene/Caprylic Capric Triglyceride Nanoemulsions Containing Isosorbide Dinitrate or Famotidine The nanoemulsions were prepared following the procedure described below.

Preparation of the Aqueous Phase of the Nanoemulsions

A combination of 150 gm of purified water, 150 gm of urea, and 40 gm of propylene glycol was mixed by constant manual stirring in a 500-ml beaker at 65-75° C. to form the aqueous phase.

Preparation of the Oil Phase of the Nanoemulsions

A combination of 80 gm of squalene, 80 gm of caprylic capric triglyceride, 16 gm of stearic acid, 14 gm of sorbitan monostearate, 40 gm of polyoxyethylene glycol (40) stearate, and 40 gm of PEG-40 hydrogenated castor oil was mixed by constant manual stirring in a 500-ml beaker at 65-75° C. to form the oil phase.

Preparation of the Nanoemulsions 150 gm of a w/o nanoemulsion composed of 60 gm of the aqueous phase and 90 gm of the oil phase was prepared following the procedure described in Example 2.

150 gm of an o/w nanoemulsion composed of 90 gm of the aqueous phase and 60 gm of the oil was prepared following the procedure described in Example 2.

150 gm of an o/w nanoemulsion composed of 88.5 gm of the aqueous phase and 60 gm of the oil phase dissolving 1.5 gm of isosorbide dinitrate was prepared following the procedure described in Example 2.

150 gm of an o/w nanoemulsion composed of 88.5 gm of the aqueous phase and 60 gm of the oil phase dissolving 1.5 gm of famotidine was prepared following the procedure described in Example 2.

All of the above nanoemulsions were clear and stable at room temperature for at least 3 months. They exhibited the Tyndall light refraction effect.

The type of each nanoemulsion prepared in this example was determined following the procedure described in Example 1.

An antimicrobial test was conducted following the procedure described in USP 35<51>, Antimicrobial Effectiveness Testing, at page 52, and all of the nanoemulsions prepared in this example passed this antimicrobial test.

Example 17: Preparation of Synthetic Oil Nanoemulsions Containing Curcumin or Testosterone The nanoemulsions were prepared following the procedure described below.

Preparation of the Aqueous Phase of the Nanoemulsions

A combination of 150 gm of purified water, 150 gm of urea, and 40 gm of propylene glycol was mixed by constant manual stirring in a 500-ml beaker at 65-75° C. to form the aqueous phase.

Preparation of the Oil Phase of a Nanoemulsion

A combination of 80 gm of caprylic capric triglyceride, 40 gm of ethyl oleate, 40 gm of sorbitan oleate, 8 gm of beeswax, 8 gm of lauric acid, 8 gm of sorbitan monostearate, and 64 gm of polyoxyethylene glycol (40) stearate was mixed in a 400-ml beaker by constant manual stirring in a 400-ml beaker at 65-75° C. to form the oil phase.

Preparation of the Nanoemulsions 135 gm of a w/o nanoemulsion composed of 45 gm of the aqueous phase and 90 gm of the oil phase was prepared following the procedure described in Example 2.

135 gm of a w/o nanoemulsion composed of 45 gm of the aqueous phase and 88.2 gm of the oil phase dissolving 1.8 gm of testosterone was prepared following the procedure described in Example 2.

135 gm of a w/o nanoemulsion composed of 45 gm of the aqueous phase and 89.4 gm of the oil phase dissolving 0.6 gm of curcumin was prepared following the procedure described in Example 2.

All of the above nanoemulsions were clear and stable at room temperature for at least 3 months. They exhibited the Tyndall light refraction effect.

The type of each nanoemulsion prepared in this example was determined following the procedure described in Example 1.

An antimicrobial test was conducted following the procedure described in USP 35<51>, Antimicrobial Effectiveness Testing, at page 52, and all of the nanoemulsions prepared in this example passed this antimicrobial test.

Example 18: Preparation of a Nanoemulsion Containing CoQ10, Vitamin A, Vitamin E, and Vitamin D The nanoemulsion was prepared following the procedure described below.

Preparation of the Aqueous Phase of the Nanoemulsion

A combination of 280 gm of purified water, 240 gm of glycerin, 48 gm of urea, and 32 gm of trehalose was mixed by constant manual stirring in a 500-ml beaker at 65-75° C. to form 600 gm of the aqueous phase.

Preparation of the Oil Phase of the Nanoemulsion

A combination of 2.4 gm of CoQ10, 4.8 gm of vitamin A, 1.2 gm of vitamin D 1.2, 30 gm of vitamin E, 85.6 gm of paraffin oil, 140 gm of cyclomethicone (DC-345), 32 gm of stearic acid, 24 gm of sorbitan stearate, and 80 gm of polyethylene glycol sorbitan monostearate was mixed by constant manual stirring in a 400-ml beaker at 65-75° C. to form 400 gm of the oil phase.

Preparation of the Nanoemulsion 1000 gm of the nanoemulsion composed of 600 gm of the aqueous phase and 400 gm of the oil phase was prepared following the procedure described in Example 2.

The above nanoemulsion was a clear o/w nanoemulsion and stable at room temperature for at least 3 months. It exhibited the Tyndall light refraction effect.

The type of the nanoemulsion was determined following the procedure described in Example 1.

An antimicrobial test was conducted following the procedure described in USP 35 <51>, Antimicrobial Effectiveness Testing, at page 52, and the nanoemulsion passed this antimicrobial test.

Example 19: Preparation of a Vitamin E/Grape Seed Oil/Coconut/Mink Oil/Paraffin Oil/Cyclomethicon Nanoemulsion The nanoemulsion was prepared following the procedure described below.

Preparation of the Aqueous Phase of the Nanoemulsion

A combination of 168 gm of purified water, 115 gm of urea, 77 gm of glycerin, 20 gm of propylene glycol, 20 gm of sodium pyrrolidone carboxylate, and 20 gm of trehalose was mixed by constant manual stirring in a 500-ml beaker at 65-75° C. to form 420 gm of the aqueous phase.

Preparation of the Oil Phase of the Nanoemulsion

A combination of 30 gm of vitamin E, 30 gm of grape seed oil, 40 gm of coconut oil, 8 gm of mink oil, 24 gm of paraffin oil, 60 gm of cyclomethicone (DC-345), 16 gm of beeswax, 8 gm of glyceryl monostearate, 19 gm of stearic acid, 17 gm of sorbitan monostearate, 50 gm of PEG-40 hydrogenated castor oil, and 28 gm of polyoxyethylene glycol (40) stearate was mixed by constant manual stirring in a 400-ml beaker at 65-75° C. to form 330 gm of the oil phase.

Preparation of the Nanoemulsion 750 gm of the nanoemulsion composed of 420 gm of the aqueous phase and 330 gm of the oil phase was prepared following the procedure described in Example 2.

The above nanoemulsion was a clear o/w nanoemulsion and stable at room temperature for at least 3 months. It exhibited the Tyndall light refraction effect.

The type of the nanoemulsion was determined following the procedure described in Example 1.

An antimicrobial test was conducted following the procedure described in USP 35 <51>, Antimicrobial Effectiveness Testing, at page 52, and the nanoemulsion passed this antimicrobial test.

Example 20: Preparation of a Vitamin E/Grape Seed Oil/Coconut/Mink Oil/Paraffin Oil/Cyclomethicon Nanoemulsion The nanoemulsion was prepared following the procedure described below.

Preparation of the Aqueous Phase of the Nanoemulsion

A combination of 168 gm of purified water, 115 gm of urea, 77 gm of glycerin, 20 gm of propylene glycol, 20 gm of sodium pyrrolidone carboxylate, and 20 gm of trehalose was mixed by constant manual stirring in a 500-ml beaker at 65-75° C. to form 420 gm of the aqueous phase.

Preparation of the Oil Phase of the Nanoemulsion

A combination of 30 gm of vitamin E, 30 gm of grape seed oil, 40 gm of coconut oil, 8 gm of mink oil, 24 gm of paraffin oil, 60 gm of cyclomethicone (DC-345), 16 gm of beeswax, 8 gm of glyceryl monostearate, 19 gm of stearic acid, 17 gm of sorbitan monostearate, 50 gm of PEG-40 hydrogenated castor oil, and 28 gm of polyethylene glycol sorbitan monostearate was mixed by constant manual stirring in a 400-ml beaker at 65-75° C. to form 330 gm of the oil phase.

Preparation of the Nanoemulsion 750 gm of the nanoemulsion composed of 420 gm of the aqueous phase and 330 gm of the oil phase was prepared following the procedure described in Example 2.

The above nanoemulsion was a clear o/w nanoemulsion and stable at room temperature for at least 3 months. It exhibited the Tyndall light refraction effect.

The type of the nanoemulsion was determined following the procedure described in Example 1.

An antimicrobial test was conducted following the procedure described in USP 35 <51>, Antimicrobial Effectiveness Testing, at page 52, and the nanoemulsion passed this antimicrobial test.

Example 21: Preparation of a Vitamin E/Grape Seed Oil/Coconut/Mink Oil/Paraffin Oil/Cyclomethicon Nanoemulsion The nanoemulsion was prepared following the procedure described below.

Preparation of the Aqueous Phase of the Nanoemulsion

A combination of 168 gm of purified water, 115 gm of urea, 77 gm of glycerin, 20 gm of propylene glycol, 20 gm of sodium pyrrolidone carboxylate, and 20 gm of trehalose was mixed by constant manual stirring in a 500-ml beaker at 65-75° C. to form 420 gm of the aqueous phase.

Preparation of the Oil Phase of the Nanoemulsion

A combination of 30 gm of vitamin E, 30 gm of grape seed oil, 40 gm of coconut oil, 8 gm of mink oil, 24 gm of paraffin oil, 60 gm of cyclomethicone (DC-345), 16 gm of beeswax, 8 gm of glyceryl monostearate, 19 gm of stearic acid, 17 gm of sorbitan monostearate, 50 gm of PEG-40 hydrogenated castor oil, and 28 gm of polyoxyethylene sorbitan monooleate was mixed by constant manual stirring in a 400-ml beaker at 65-75° C. to form 330 gm of the oil phase.

Preparation of the Nanoemulsion 750 gm of the nanoemulsion composed of 420 gm of the aqueous phase and 330 gm of the oil phase was prepared following the procedure described in Example 2.

The above nanoemulsion was a clear o/w nanoemulsion and stable at room temperature for at least 3 months. It exhibited the Tyndall light refraction effect.

The type of the nanoemulsion was determined following the procedure described in Example 1.

An antimicrobial test was conducted following the procedure described in USP 35 <51>, Antimicrobial Effectiveness Testing, at page 52, and the nanoemulsion passed this antimicrobial test.

Example 22: Preparation of a Vitamin E/Grape Seed Oil/Coconut/Mink Oil/Paraffin Oil/Cyclomethicon Nanoemulsion The nanoemulsions was prepared following the procedure described below.

Preparation of the Aqueous Phase of the Nanoemulsion

A combination of 150 gm of purified water, 150 gm of urea, and 40 gm of propylene glycol was mixed by constant manual stirring in a beaker at 65-75° C. to form 340 gm of the aqueous phase.

Preparation of the Oil Phase of the Nanoemulsion

A combination of 30 gm of vitamin E, 30 gm of grape seed oil, 40 gm of coconut oil, 8 gm of mink oil, 24 gm of paraffin oil, 60 gm of cyclomethicone (DC-345), 16 gm of beeswax, 8 gm of glyceryl monostearate, 19 gm of stearic acid, 17 gm of sorbitan monostearate, 50 gm of PEG-40 hydrogenated castor oil, and 28 gm of polyoxyethylene glycol (40) stearate was mixed by constant manual stirring in a 400-ml beaker at 65-75° C. to form 330 gm of the oil phase.

Preparation of the Nanoemulsion 750 gm of the nanoemulsion composed of 420 gm of the aqueous phase and 330 gm of the oil phase was prepared following the procedure described in Example 2.

The above nanoemulsion was a clear o/w nanoemulsion and stable at room temperature for at least 3 months. It exhibited the Tyndall light refraction effect.

The type of the nanoemulsion was determined following the procedure described in Example 1.

An antimicrobial test was conducted following the procedure described in USP 35<51>, Antimicrobial Effectiveness Testing, at page 52, and the nanoemulsion passed this antimicrobial test.

Example 23: Preparation of Essential Oil Nanoemulsions Containing Only One Hydrophilic Surfactant The nanoemulsions were prepared following the procedure described below.

Preparation of the Aqueous Phase of the Nanoemulsions

A combination of 200 gm of purified water, 100 gm of glycerin, 50 gm of glucosamine, and 50 gm of methyl sulfonyl methane was mixed by constant manual stirring in a 500-ml beaker at 65-75° C. to form the aqueous phase.

Preparation of the Oil Phase of the Nanoemulsions

A combination of 30 gm of vitamin E, 30 gm of grape seed oil 30 gm, 40 gm of coconut oil, 8 gm of mink oil, 24 gm of paraffin oil, 60 gm of cyclomethicon (DC-345), 16 gm of beeswax, 8 gm of glyceryl monostearate, 19 gm of stearic acid, 17 gm of sorbitan monostearate, and 68 gm of PEG-40 hydrogenated castor oil was mixed by constant manual stirring in a 400-ml beaker at 65-75° C. to form the oil phase.

Preparation of the Nanoemulsions 150 gm of a w/o nanoemulsion composed of 60 gm of the aqueous phase and 90 gm of the oil phase was prepared following the procedure described in Example 2.

150 gm of an o/w nanoemulsion composed of 90 gm of the aqueous phase and 60 gm of the oil phase was prepared following the procedure described in Example 2.

The above nanoemulsions were clear and stable at room temperature for at least 3 months. They exhibited the Tyndall light refraction effect.

The type of each nanoemulsion prepared in this example was determined following the procedure described in Example 1.

An antimicrobial test was conducted following the procedure described in USP 35 <51>, Antimicrobial Effectiveness Testing, at page 52, and the two nanoemulsions prepared in this example passed this antimicrobial test.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A nanoemulsion comprising:
   (A) an aqueous phase including:
      (1) water or a water solution, and
      (2) one or more water-soluble organic nanostructure stabilizers, in which the water or water solution has a content less than 75% by weight of the aqueous phase, each of the water-soluble organic nanostructure stabilizers has a content less than 99% by weight of the aqueous phase, and at least one of the water-soluble organic nanostructure stabilizers is urea, xylitol, or glucosamine, and
   (B) an oil phase including:
      (1) an oil or an oil solution,
      (2) an organic gel thickener, and
      (3) a hydrophilic surfactant having a hydrophilic-lipophilic balance value greater than 8.0,
in which the oil or oil solution has a content less than 80% by weight of the oil phase, the organic gel thickener has a content less than 60% by weight of the oil phase, and the hydrophilic surfactant has a content less than 60% by weight of the oil phase, wherein the water or water solution constitutes 2.5% by weight or more of the nanoemulsion, a weight ratio of the aqueous phase to the oil phase is 1:40-100:1, the aqueous phase is dispersed as nanosized droplets in the oil phase or the oil phase is dispersed as nanosized droplets in the aqueous phase, and the nanoemulsion is self-preserving, in the absence of an anti-microbial preservative, and has reversible continuous and dispersed phases.

2. The nanoemulsion of claim 1, wherein the oil phase is dispersed as the nanosized droplets in the aqueous phase.

3. The nanoemulsion of claim 1, wherein the aqueous phase is dispersed as the nanosized droplets in the oil phase.

4. The nanoemulsion of claim 2, wherein the hydrophilic-lipophilic balance value is greater than 10.

5. The nanoemulsion of claim 4, wherein the hydrophilic-lipophilic balance value is greater than 13.

6. The nanoemulsion of claim 3, wherein the hydrophilic-lipophilic balance value is greater than 10.

7. The nanoemulsion of claim 6, wherein the hydrophilic-lipophilic balance value is greater than 13.

8. The nanoemulsion of claim 4, wherein the water-soluble organic nanostructure stabilizer is a water-soluble vitamin, a water-soluble peptide, a water-soluble oligopeptide, a polyol, a water-soluble saccharide, a water-soluble oligosaccharide, a disaccharide, a mono-saccharides, a hydrogenated carbohydrate, an amino acid, amino sugar, or a combination thereof; the oil is a vegetable oil, a silicone oil, a synthetic oil, a mineral oil, an animal oil, an essential oil, or a combination thereof; and the organic gel thickener is saturated fatty acid, fatty acid alcohol, a fatty acid derivative having a melting point above 45° C., or a combination thereof.

9. The nanoemulsion of claim 4, wherein, also among the water-soluble organic nanostructure stabilizers, if any, is methylsulfonylmethane, hydroxyethyl urea, mannitol, sorbitol, lactose, fructose, dextrose, ribose, trehalose, raffinose, maltitol, isomalt, lactitol, erythritol, inositol, taurine, glycerin, propylene glycol, dipropylene glycol, butylene glycol, hexylene glycol, polyethylene glycol, ethoxydiglycol, carnitine, arginine, sodium pyrrolidone carboxylic acid, and hydrolyzed collagen, or a combination thereof; the oil is coconut oil, palm oil, grape seed oil, grape fruit seed oil, olive oil, avocado oil, evening primrose oil, tea tree oil, eucalyptus oil, lavender oil, rosemary oil, horse fat, fish oil, squalene, lanolin oil, squalene, cyclomethicone, cyclopentasiloxane, phenyl trimethicone, caprylic or capric triglyceride, isopropyl myristate, isostearyl isostearate, decyl oleate, ethylhexyl isononanoate, isohexadecane, octyldodecanol, paraffin oil, polyisobutene, polydecene, menthol, or a combination thereof; the organic gel thickener is stearic acid, lauric acid, glycerol monostearate, PEG 6000 Distearate, monoglyceride, diglyceride, saccharide fatty acid ester, propylene glycol fatty acid ester, glycol fatty acid ester, hexyl decyl fatty acid ester, fatty acid alcohol, cetyl stearate, ascorbyl fatty ester, glyceryl fatty ester, hexyldecyl fatty ester, or a combination thereof; and the hydrophilic surfactant is polyoxyethylene sorbitan fatty acid ester, polyoxyethylene sorbitol fatty acid ester, polyoxyethylene fatty acid ester, polyoxyethylene alcohol ester, nonyl phenol alkoxylate, alkyl alkoxylate, poly(ethylene glycol)-poly(propylene glycol)-poly(ethylene glycol) copolymer, PEG dimethicone, polyoxyethylene (40) fatty acid ester, polyoxyethylene (20) saccharide fatty acid ester, PEG-15 glyceryl fatty acid ester, PEG-35 hydrogenated castor oil, PEG-40 hydrogenated castor oil, polyglycerol fatty acid ester, fatty amine derivative, or a combination thereof.

10. The nanoemulsion of claim 9, wherein the hydrophilic-lipophilic balance value is greater than 13; the water or water solution has a content less than 60% by weight of the aqueous phase and the water-soluble organic nanostructure stabilizer has a content less than 50% by weight of the aqueous phase; the oil or oil solution has a content less than 45-65% by weight of the oil phase, the organic gel thickener has a content less than 25% by weight of the oil phase, and the hydrophilic surfactant has a content less than 35% by weight of the oil phase; the water or water solution constitutes 30% by weight or less of the nanoemulsion and a weight ratio of the aqueous phase to the oil phase is 1:2-3:1; and the nanoemulsion has a pH of 3-11 and is transparent or translucent.

11. The nanoemulsion of claim 6, wherein the water-soluble organic nanostructure stabilizer is a water-soluble vitamin, a water-soluble peptide, a water-soluble oligopepetide, a polyol, a water-soluble saccharide, a water-soluble oligosaccharide, a disaccharide, a mono-saccharides, a hydrogenated carbohydrate, an amino acid, amino sugar, or a combination thereof; the oil is a vegetable oil, a silicone oil, a synthetic oil, a mineral oil, an animal oil, an essential oil, or a combination thereof; and the organic gel thickener is saturated fatty acid, fatty acid alcohol, a fatty acid derivative having a melting point above 45° C., or a combination thereof.

12. The nanoemulsion of claim 6, wherein, also among the water-soluble organic nanostructure stabilizers, if any, is methylsulfonylmethane, hydroxyethyl urea, mannitol, sorbitol, lactose, fructose, dextrose, ribose, trehalose, raffinose, maltitol, isomalt, lactitol, erythritol, inositol, taurine, glycerin, propylene glycol, dipropylene glycol, butylene glycol, hexylene glycol, polyethylene glycol, ethoxydiglycol, carnitine, arginine, sodium pyrrolidone carboxylic acid, and hydrolyzed collagen, or a combination thereof; the oil is coconut oil, palm oil, grape seed oil, grape fruit seed oil, olive oil, avocado oil, evening primrose oil, tea tree oil, eucalyptus oil, lavender oil, rosemary oil, horse fat, fish oil, squalene, lanolin oil, squalene, cyclomethicone, cyclopentasiloxane, phenyl trimethicone, caprylic or capric triglyceride, isopropyl myristate, isostearyl isostearate, decyl oleate, ethylhexyl isononanoate, isohexadecane, octyldodecanol, paraffin oil, polyisobutene, polydecene, menthol, or a combination thereof; the organic gel thickener is stearic acid, lauric acid, glycerol monostearate, PEG 6000 Distearate, monoglyceride, diglyceride, saccharide fatty acid ester, propylene glycol fatty acid ester, glycol fatty acid ester, hexyl decyl fatty acid ester, fatty acid alcohol, cetyl stearate, ascorbyl fatty acid ester, glyceryl fatty ester, hexyldecyl fatty ester, or a combination thereof; and the hydrophilic surfactant is polyoxyethylene sorbitan fatty acid ester, polyoxyethylene sorbitol fatty acid ester, polyoxyethylene fatty acid ester, polyoxyethylene alcohol ester, nonyl phenol alkoxylate, alkyl alkoxylate, poly(ethylene glycol)-poly(propylene glycol)-poly(ethylene glycol) copolymer, PEG dimethicone, polyoxyethylene (40) fatty acid ester, polyoxyethylene (20) saccharide fatty acid ester, PEG-15 glyceryl fatty acid ester, PEG-35 hydrogenated castor oil, PEG-40 hydrogenated castor oil, polyglycerol fatty acid ester, fatty amine derivative, or a combination thereof.

13. The nanoemulsion of claim 12, wherein the hydrophilic-lipophilic balance value is greater than 13; the water or water solution has a content less than 60% by weight of the aqueous phase and the water-soluble organic nanostructure stabilizer has a content less than 50% by weight of the aqueous phase; the oil or oil solution has a content less than 45-65% by weight of the oil phase, the organic gel thickener has a content less than 25% by weight of the oil phase, and the hydrophilic surfactant has a content less than 35% by weight of the oil phase; the water or water solution constitutes 30% by weight or less of the nanoemulsion and a weight ratio of the aqueous phase to the oil phase is 1:2-3:1; and the nanoemulsion has a pH of 3-11 and is transparent or translucent.

14. The nanoemulsion of claim 8, wherein the water or water solution has a content less than 60% by weight of the aqueous phase and the water-soluble organic nanostructure stabilizer has a content less than 70% by weight of the aqueous phase; the oil or oil solution has a content 30-70% by weight of the oil phase, the organic gel thickener has a content less than 45% by weight of the oil phase, and the hydrophilic surfactant has a content less than 45% by weight of the oil phase; and the water or water solution constitutes 38% by weight or less of the nanoemulsion and a weight ratio of the aqueous phase to the oil phase is 1:3-4:1.

15. The nanoemulsion of claim 14, wherein the water or water solution has a content less than 45% by weight of the aqueous phase and the water-soluble organic nanostructure stabilizer has a content less than 50% by weight of the aqueous phase; the oil or oil solution has a content less than 45-65% by weight of the oil phase, the organic gel thickener has a content less than 25% by weight of the oil phase, and the hydrophilic surfactant has a content less than 35% by weight of the oil phase; and the water or water solution constitutes 30% by weight or less of the nanoemulsion and a weight ratio of the aqueous phase to the oil phase is 1:2-3:1.

16. The nanoemulsion of claim 11, wherein the water or water solution has a content less than 60% by weight of the aqueous phase and the water-soluble organic nanostructure stabilizer has a content less than 70% by weight of the aqueous phase; the oil or oil solution has a content 30-70% by weight of the oil phase, the organic gel thickener has a content less than 45% by weight of the oil phase, and the hydrophilic surfactant has a content less than 45% by weight of the oil phase; and the water or water solution constitutes 38% by weight or less of the nanoemulsion and a weight ratio of the aqueous phase to the oil phase is 1:3-4:1.

17. The nanoemulsion of claim 16, wherein the water or water solution has a content less than 45% by weight of the aqueous phase and the water-soluble organic nanostructure stabilizer has a content less than 50% by weight of the aqueous phase; the oil or oil solution has a content less than 45-65% by weight of the oil phase, the organic gel thickener has a content less than 25% by weight of the oil phase, and the hydrophilic surfactant has a content less than 35% by weight of the oil phase; and the water or water solution constitutes 30% by weight or less of the nanoemulsion and a weight ratio of the aqueous phase to the oil phase is 1:2-3:1.

18. The nanoemulsion of claim 15, wherein the nanoemulsion has a pH of 3-11 and is transparent or translucent.

19. The nanoemulsion of claim 17, wherein the nanoemulsion has a pH of 3-11 and is transparent or translucent.

20. The nanoemulsion of claim 1, wherein the nanoemulsion has a pH of 3-11 and is transparent or translucent.

21. The nanoemulsion of claim 1, wherein the nanoemulsion is a cosmetic product, a pharmaceutical product, a food product, a household chemical product, an agricultural product, a printing product, a dying product, a veterinary product, or a diagnostic product.

22. A method for preparing the nanoemulsion of claim 1, the method comprising:
(1) mixing water or a water solution and one or more water-soluble organic nanostructure stabilizers to form an aqueous phase, in which the water or water solution has a content less than 75% by weight of the aqueous phase and each of the water-soluble organic nanostructure stabilizers has a content less than 99% by weight of the aqueous phase, and at least one of the water-soluble organic nanostructure stabilizers is urea, xylitol, or glucosamine;

(2) mixing an oil or an oil solution, an organic thickener, and a hydrophilic surfactants having a hydrophilic-lipophilic balance value greater than 8.0 to form an oil phase, in which the oil or oil solution has a content less than 80% by weight of the oil phase, the organic gel thickener has a content less than 60% by weight of the oil phase, and the hydrophilic surfactant has a content less than 60% by weight of the oil phase; and (3) mixing the aqueous phase and the oil phase, a weight ratio of the aqueous phase to the oil phase being 1:40-100:1, to form a nanoemulsion, in which the water or water solution constitutes 74% by weight or less of the nanoemulsion;

whereby the aqueous phase is dispersed as nanosized droplets in the oil phase or the oil phase is dispersed as nanosized droplets in the aqueous phase.

* * * * *